(12) United States Patent
Zhang

(10) Patent No.: US 10,322,281 B2
(45) Date of Patent: Jun. 18, 2019

(54) ADJUSTABLE ANGLE NEURO STIMULATION PROBE APAPRATUS

(71) Applicant: Xialing Zhang, Mountain View, CA (US)

(72) Inventor: Xialing Zhang, Mountain View, CA (US)

( * ) Notice: Subject to any disclaimer, the term of this patent is extended or adjusted under 35 U.S.C. 154(b) by 0 days.

(21) Appl. No.: 15/619,485

(22) Filed: Jun. 11, 2017

(65) Prior Publication Data

US 2018/0147410 A1  May 31, 2018

Related U.S. Application Data

(60) Provisional application No. 62/426,484, filed on Nov. 26, 2016.

(51) Int. Cl.
*A61B 5/00* (2006.01)
*A61N 1/05* (2006.01)
(Continued)

(52) U.S. Cl.
CPC .............. *A61N 1/36* (2013.01); *A61B 5/4076* (2013.01); *A61B 5/4893* (2013.01);
(Continued)

(58) Field of Classification Search
CPC .... A61N 1/36; A61N 1/0531; A61N 1/36017; A61N 1/0551; A61B 5/4076;
(Continued)

(56) References Cited

U.S. PATENT DOCUMENTS

| 4,602,624 A | 7/1986 | Naples et al. |
| 5,242,441 A * | 9/1993 | Avitall ............... A61B 18/1492 600/374 |

(Continued)

FOREIGN PATENT DOCUMENTS

| EP | 0753284 A2 | 1/1997 |
| WO | 2001028622 A2 | 4/2001 |

(Continued)

OTHER PUBLICATIONS

International Search Report and Written Opinion, dated Jan. 29, 2018, PCT/US17/62061.

*Primary Examiner* — Catherine M Voorhees
(74) *Attorney, Agent, or Firm* — David O. Simmons; IVC Patent Agency

(57) ABSTRACT

A stimulation probe apparatus as provided herein offers adjustability of a conductive probe tip thereof relative to a handle assembly thereof to which the conductive probe tip is physically attached. The adjustability of the conductive probe tip relative to the handle assembly provide for a surgeon's ability to selectively orientate the conductive probe tip with respect to the handle assembly for enabling a desired placement of the conductive probe tip relative to the handle assembly. In this respect, by allowing a surgeon to selectively control the direction of the conductive probe tip to point in a desired angle, embodiments of the present invention serve clinical needs that help surgeon to perform electrophysiological testing in diverse anatomical structures and in diverse operation procedures.

10 Claims, 3 Drawing Sheets

(51) Int. Cl.
*A61N 1/36* (2006.01)
*A61B 17/00* (2006.01)
*A61B 18/00* (2006.01)

(52) U.S. Cl.
CPC .. *A61N 1/0531* (2013.01); *A61B 2017/00039* (2013.01); *A61B 2018/00839* (2013.01); *A61N 1/0551* (2013.01); *A61N 1/36017* (2013.01)

(58) Field of Classification Search
CPC .......... A61B 2017/0069; A61B 5/4893; A61B 2018/00839; A61B 2017/00039
See application file for complete search history.

(56) References Cited

U.S. PATENT DOCUMENTS

| | | | |
|---|---|---|---|
| 5,545,200 A * | 8/1996 | West | A61B 18/1492 |
| | | | 606/29 |
| 5,643,255 A | 7/1997 | Organ | |
| 5,824,027 A | 10/1998 | Hoffer et al. | |
| 5,857,980 A | 1/1999 | Wilson | |
| 5,913,882 A | 6/1999 | King | |
| 6,241,728 B1 | 6/2001 | Gaiser et al. | |
| 6,529,774 B1 | 3/2003 | Greene | |
| 7,167,751 B1 | 1/2007 | Whitehurst et al. | |
| 7,310,557 B2 | 12/2007 | Maschino | |
| 7,561,918 B2 | 7/2009 | Armstrong et al. | |
| 7,878,981 B2 * | 2/2011 | Strother | A61B 17/1626 |
| | | | 600/554 |
| 2002/0183817 A1 | 12/2002 | Van Venrooij | |
| 2003/0040785 A1 | 2/2003 | Maschino | |
| 2004/0010303 A1 | 1/2004 | Bolea et al. | |
| 2005/0137645 A1 | 6/2005 | Voipio | |
| 2006/0030919 A1 | 2/2006 | Mrva et al. | |
| 2006/0167497 A1 | 7/2006 | Armstrong et al. | |
| 2008/0046016 A1 | 2/2008 | Ben-David et al. | |
| 2008/0319314 A1 | 12/2008 | Hill et al. | |
| 2014/0246471 A1 * | 9/2014 | Jaworek | A61B 17/068 |
| | | | 227/175.1 |

FOREIGN PATENT DOCUMENTS

| | | |
|---|---|---|
| WO | 2004034880 A2 | 4/2004 |
| WO | 2004087256 A2 | 10/2004 |
| WO | 2006017277 A2 | 2/2006 |
| WO | 2006041870 A2 | 4/2006 |
| WO | 2007064739 A2 | 6/2007 |

* cited by examiner

ADJUSTABLE ANGLE NEURO STIMULATION PROBE APAPRATUS

CROSS-REFERENCE TO RELATED APPLICATIONS

This non-provisional patent application claims priority from U.S. Provisional Patent Application having Ser. No. 62/426,484, filed 26 Nov. 2016, entitled "ANGLE-CONTROLLER NEURO STIMULATION PROBES", having a common applicant herewith and being incorporated herein in its entirety by reference.

FIELD OF THE DISCLOSURE

The disclosures made herein relate generally to implements for neurological and neurophysiological studies, techniques and apparatuses and, more particularly, to an adjustable angle neuro stimulation probe apparatus that is a useful implement for neurological and neurophysiological studies.

BACKGROUND

Neuro and orthopedic surgeries are well known. It is also well known that, in these types of surgical procedures, surgeon often need to perform electrophysiological (e.g., neurophysiological) testing onto target tissue or subject to verify its involvement of neural function. Such electrophysiological testing is performed to reduce the risk of nerve permanent injury and to improve surgical outcome.

A stimulation probe apparatus is an implement used by a surgeon during electrophysiological testing (e.g., for neuronal functional/or diagnostic testing). The stimulation probe apparatus comprises a conductive probe tip and a handle assembly to which the conductive probe tip is physically attached for allowing a surgeon to manipulate the conductive probe tip. The conductive probe tip, which can disposable or re-usable, is electrically connected to an electrophysiological system machine, neuronal diagnostic system, or other type of test system for enabling a stimulation current (i.e., electrical current) to be delivered from the attached test system via the conductive probe tip to tissue being tested (i.e., the subject tissue), an implant being tested, and/or the like. In response to the stimulation current being delivered from the conductive probe tip, the attached test system or other system receives and assesses (e.g., quantifies) a response signal (e.g., neural response(s) to the current delivered). Such testing aims to verify the involvement of electrophysiological (e.g., neuronal) functions within the tissue being tested and to determine safe thresholds for preventing functional tissue from being damaged. It is common for electrophysiological testing to be continuously performed during the surgeries to avoid surgical manipulation or injury of tissue that can lead to permanent damage to its electrophysiological functions.

Capabilities of conventional stimulation probe apparatuses do not satisfy current needs of surgeons. Specifically, conventional stimulation probe apparatuses have a fixed conductive probe tip orientation with respect to the handle assembly. This fixed orientation of the conductive probe tip relative to the handle assembly limits a surgeon's ability to selectively orientate the conductive probe tip with respect to the handle assembly for enabling a desired placement of the conductive probe tip relative to the handle assembly. Therefore, a stimulation probe apparatus offering adjustability of the conductive probe tip relative to the handle assembly would overcomes drawbacks associated with conventional stimulation probe apparatuses and would thereby be advantageous, desirable and useful.

SUMMARY OF THE DISCLOSURE

Embodiments of the present invention are directed to a stimulation probe apparatus useful to surgeons during electrophysiological testing. More specifically, embodiments of the present invention are directed to a stimulation probe apparatus offering adjustability of a conductive probe tip thereof relative to a handle assembly thereof to which the conductive probe tip is physically attached. The adjustability of the conductive probe tip relative to the handle assembly provide for a surgeon's ability to selectively orientate the conductive probe tip with respect to the handle assembly for enabling a desired placement of the conductive probe tip relative to the handle assembly. In this respect, by allowing a surgeon to selectively control the direction of the conductive probe tip to point in a desired angle, embodiments of the present invention serve clinical needs that help surgeon to perform electrophysiological testing in diverse anatomical structures and in diverse operation procedures. Thus, embodiments of the present invention advantageously overcome one or more shortcomings associated with conventional stimulation probe apparatuses, which have a fixed conductive probe tip orientation with respect to the handle assembly.

In one embodiment of the present invention, an electrophysiological test stimulation probe apparatus comprises a conductive probe tip and a stimulation probe handle assembly. The stimulation probe handle assembly includes a main body and a tip adjustment structure attached to the main body. The tip adjustment structure is rotatable with respect to the main body about a longitudinal axis of the main body. The conducting probe is attached to the tip adjustment structure. The conductive probe tip is pivotable with respect to the tip adjustment structure about a transverse axis that extends one of perpendicular to a longitudinal axis of the stimulation probe handle assembly and skewed with respect to the longitudinal axis.

In another embodiment of the present invention, an electrophysiological test stimulation probe apparatus comprising a stimulation probe tip assembly and a stimulation probe handle assembly. The stimulation probe tip assembly has a conductive probe tip and a mounting portion attached to the conductive probe tip. The stimulation probe handle assembly includes a main body, a tip adjustment structure and a stimulation current conveying structure. The tip adjustment structure is rotatably attached at a first end portion thereof to the main body for being rotated with respect to the main body about a longitudinal axis thereof. The mounting portion of the stimulation probe tip assembly is attached to the tip adjustment structure. The tip adjustment structure includes mating segments thereof that are pivotably attached to each other for enabling the conductive probe tip to be pivoted about a transverse axis that extends one of perpendicular to the longitudinal axis and skewed with respect to the longitudinal axis. The stimulation current conveying structure is mounted on the main body and is electrically connected to the conductive probe tip for enabling a stimulation current to be provided therethrough to the conductive probe tip.

In another embodiment of the present invention, a stimulation probe apparatus comprising a conductive probe tip, a stimulation probe handle, and a stimulation current conveying structure. The conductive probe tip has a first end portion and a second end portion. The stimulation probe handle has a first end portion and a second end portion. The first end portion of the conductive probe tip includes a tip adjustment structure that is attached to the first end portion of the stimulation probe handle. The tip adjustment structure is adapted to enable the conductive probe tip to be rotated with respect to the stimulation probe handle about a longitudinal axis thereof and to enable the conductive probe tip to be pivoted about an axis that extends one of perpendicular to the longitudinal axis and skewed with respect to the longitudinal axis. The stimulation current conveying structure is mounted on the stimulation probe handle and is electrically attached to the conductive probe tip for enabling a stimulation current to be provided thereto through the stimulation current conveying structure.

These and other objects, embodiments, advantages and/or distinctions of the present invention will become readily apparent upon further review of the following specification, associated drawings and appended claims.

DETAILED DESCRIPTION

Figure 1:
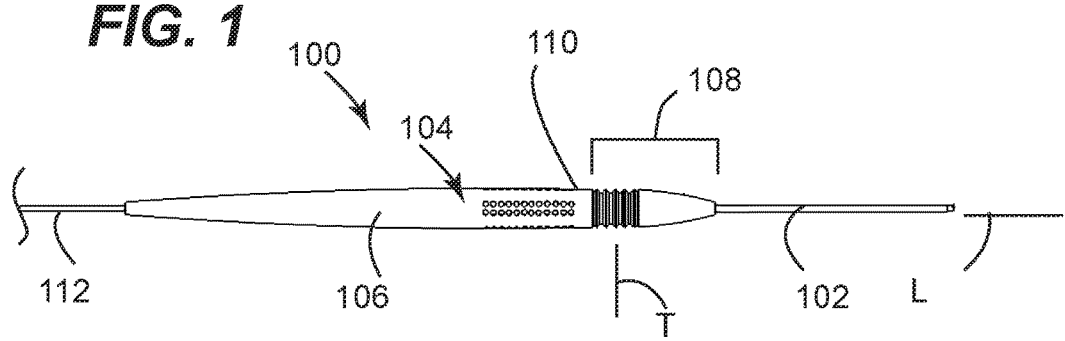
FIG. 1 is a side view of an electrophysiological test stimulation probe apparatus configured in accordance with an embodiment of the present invention.

FIGS. 1-4 shown an electrophysiological test stimulation probe apparatus 100 configured in accordance with an embodiment of the present invention. The electrophysiological test stimulation probe apparatus 100 comprises a conductive probe tip 102 and a handle assembly 104. The stimulation probe apparatus 100 offers adjustability of a conductive probe tip 102 relative to the handle assembly 104 to which the conductive probe tip 102 is physically attached. The adjustability of the conductive probe tip 102 relative to the handle assembly 104 provide for a surgeon's ability to selectively orientate the conductive probe tip with respect to the handle assembly 104 for enabling a desired placement of the conductive probe tip 102 relative to the handle assembly 104. In this respect, by allowing a surgeon to selectively control the direction of the conductive probe tip 102 to point in a desired angle, embodiments of the present invention serve clinical needs that help surgeon to perform electrophysiological testing in diverse anatomical structures and in diverse operation procedures.

The handle assembly 104 includes a main body 106 and a tip adjustment structure 108 attached to the main body 106. The tip adjustment structure 108 can be attached at a first end portion 110 of the main body 106. In some embodiments, the main body 106 can be a housing having an interior space within which apparatus components (e.g., a stimulation current conveying structure) can be located. In other embodiments, the main body 106 can be a frame having exterior surfaces upon which apparatus components can be mounted.

Figure 3:
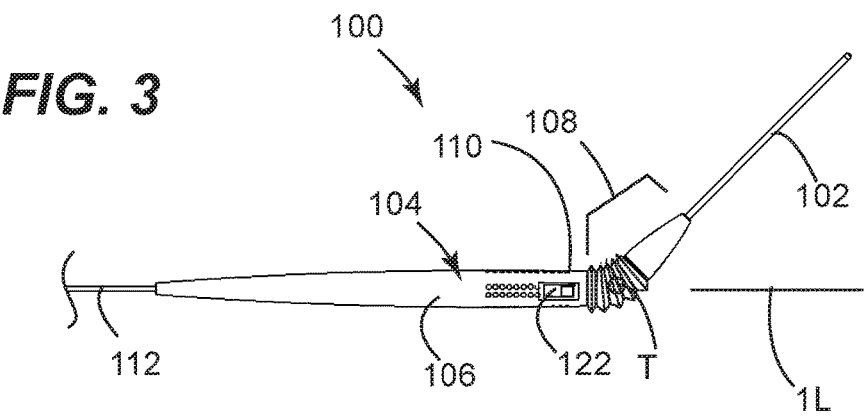
FIG. 3 is a top view of the electrophysiological test stimulation probe apparatus shown in FIG. 1, with a conductive probe tip thereof in a pivoted orientation with respect to a main body thereof.
Figure 4:
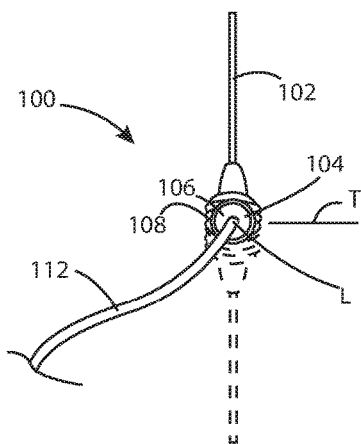
FIG. 4 is a rear view of the electrophysiological test stimulation probe apparatus shown in FIG. 1, with a conductive probe tip thereof in a pivoted and rotated orientation with respect to a main body thereof.

As best shown in FIGS. 3 and 4, the tip adjustment structure 108 enables independent rotation of the tip adjustment structure 108 and pivoting of the conducting probe tip. The tip adjustment structure 108 can be rotatably attached to the main body 106 such that the tip adjustment structure 108 can rotate with respect to the main body 106 about a longitudinal axis L of the main body 106. The longitudinal axis L of the main body 106 defines a longitudinal axis of the handle assembly 104. The tip adjustment structure 108 provides for pivoting of the conducting probe tip 102 with respect to the tip adjustment structure about a transverse axis T. In some embodiments, the transverse axis T extends perpendicular to the longitudinal axis L. In other embodiments, the transverse axis T is skewed with respect to the longitudinal axis L.

Electrophysiological test stimulation probe apparatuses configured in accordance with embodiments of the present invention are not limited a particular degree of rotational about the longitudinal axis L or particular degree of pivoting about the transverse axis T. In some embodiments, the tip adjustment structure 108 can rotate with respect to the main body 106 about the longitudinal axis L up to or less than 360 degrees. In some embodiments, the tip adjustment structure 108 can enable the conducting probe tip 102 to be pivoted with respect to the main body 106 about the transverse axis T up to or less than 90 degrees. Furthermore, the tip adjustment structure 108 can enable the conducting probe tip 102 to be pivoted in two directions about the transverse axis T, thereby allowing a total degree of pivoting up to or less than 180 degrees.

Referring back to FIGS. 1-4, the electrophysiological test stimulation probe apparatus 100 includes a signal wire 112 through which a stimulation current is provided from a test system to the conducting probe tip 102 whereby the conductive probe tip 102 is electrically coupled to the signal wire 112. In preferred embodiments, the tip adjustment structure 108 provides for electrical continuity between the signal wire 112 and the conductive probe tip 102. The present invention is not limited to any particular arrangement for providing such electrical continuity and, in view of the disclosures made herein, a skilled person will appreciate a variety of different arrangements of the tip adjustment structure 108 that provide for such electrical continuity in combination with the afore-mentioned rotational/pivoting capability.

The main body 106 is preferably made from an electrically insulating or otherwise non-conductive material for electrically insulating the main body 106 from the stimulation current. Furthermore, one or more surfaces of the main body 106 can be defined by a material that enhances tactile attributes, non-slip attributes (e.g., such as when the electrophysiological test stimulation probe apparatus 100 is exposed to liquids) or a combination thereof. Still further, one or more surfaces of the main body 106 can be contoured for enhancing non-slip attributes, tactile attributes, or a combination thereof.

Figure 5:
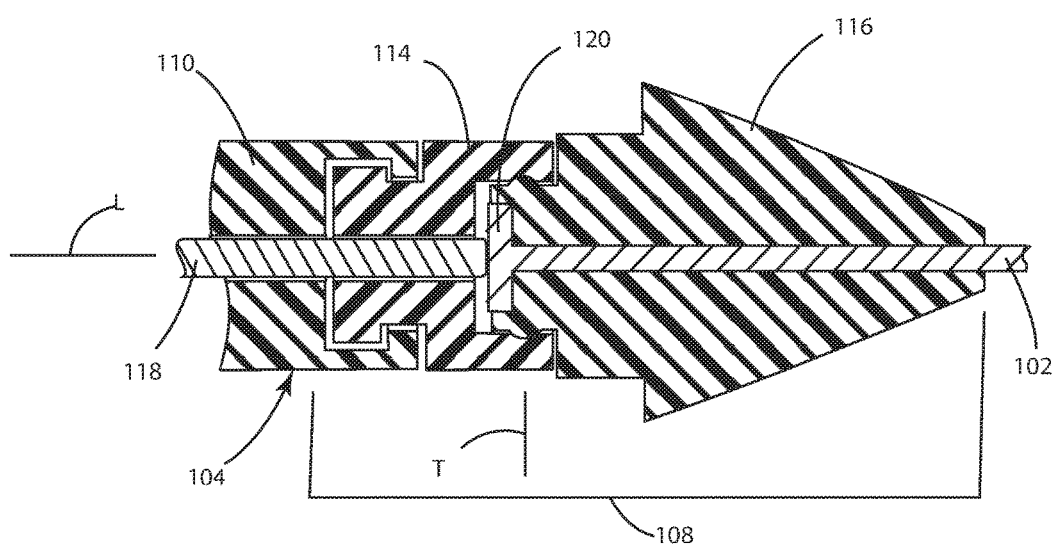
FIG. 5 is a cross-sectional view taken along the line 5-5 in FIG. 2.

In one embodiment, as best shown in FIG. 5, the tip adjustment structure 108 includes an interposer body 114 and a probe tip mount 116, as shown with optional protective bellow cover of FIGS. 1-4 omitted. The interposer body 114 has a first end portion thereof rotationally attached to the main body 106. The probe tip mount 116 is pivotably attached to a second end portion of the interposer body 114. The rotation-enabling interface between the main body 106 and the interposer body 114 and the pivot-enabling interface between the interposer body 114 and the probe tip mount 116 can have a configuration that provides sufficient friction (e.g., via interference fit or friction providing structure) for maintaining the conductive probe tip 102 in an as-set orientation during use. Alternatively, the main body 106, the interposer body 114, the probe tip mount 116 of a combination thereof can include one or more structural elements for allowing the conductive probe tip 102 to be mechanically restrained in an as-set orientation during use.

Still referring to FIG. 5, the conductive probe tip 102 is mounted on the probe tip mount 116. In one embodiment, electrical continuity can be provided through the tip adjustment structure 108 via a conductive member 118 that extends axially through the main body 106 and the interposer body 114 into electrically conductive contact with a head portion 120 of the conductive probe tip 102. For example, the conductive member 118 can be spring based and/or the conductive probe tip 102 can be spring-biased such that an end portion of the conductive member 118 is maintained in abutted-contact with the head portion 120 of the conductive probe tip 102. The signal wire 112 can be directly or indirectly attached to the conductive member 118.

In view of the disclosures herein, a skilled person will appreciate numerous approaches for providing electrical continuity between the signal wire 112 and the conductive probe tip 102. For example, in one such arrangement, the signal wire 112 can be attached directly to the conductive probe tip 102. In another such embodiment, the interposer body 114 and the probe tip mount 116 can be made from or coated with a conductive material, whereby the signal wire 112 can be attached to the interposer body 114 in a manner providing electrical conductivity therebetween and the conductive probe tip 102 can be mounted on the probe tip mount 116 in a manner providing electrical conductivity therebetween. In still another embodiment, the interposer body 114 can include a conductive member such as a wire that provides electrical continuity therethrough (e.g., connects the conductive probe tip 102 directly or indirectly to the signal wire 112.

Figure 2:
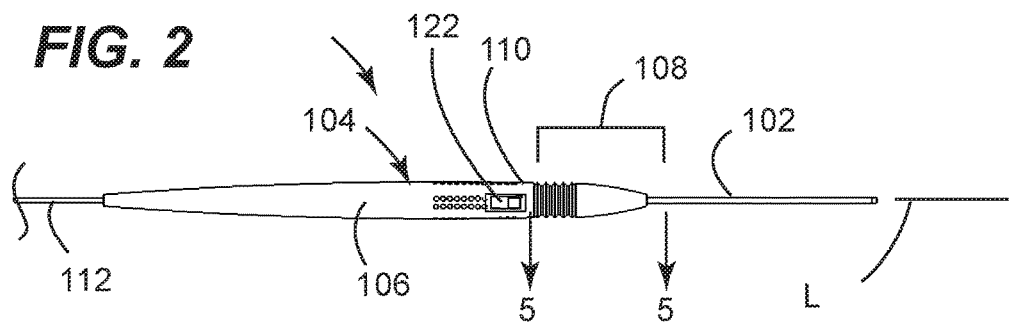
FIG. 2 is a top view of the electrophysiological test stimulation probe apparatus shown in FIG. 1.
Figure 6:
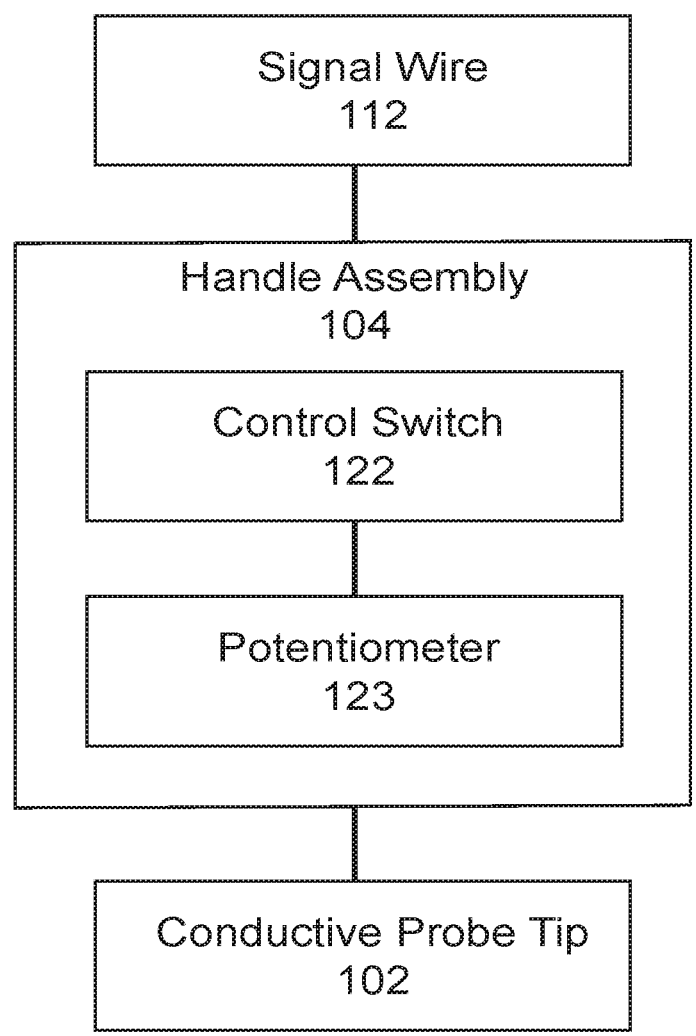
FIG. 6 is a block diagram showing an electrical continuity controller comprising a control switch and a potentiometer.

The handle assembly 104 can include a stimulation current conveying structure that is electrically connected between the conductive probe tip 102 and the signal wire 112. For example, the stimulation current conveying structure can be mounted on the main body 106 (e.g., fully or partially within an interior space thereof). The stimulation current conveying structure can include an electrical continuity controller for enabling electrical continuity between the stimulation current conveying structure and the conductive probe tip to be selectively inhibited and enabled. In one embodiment, as shown in FIGS. 2 and 3, the electrical continuity controller comprises a control switch 122. The control switch 122 can have a static position in which electrical continuity is enable and displaced position in which continuity is inhibited (or vice versa). It is disclosed herein that the control switch 122 can be a momentary switch or a slider switch. Furthermore, the control switch 122 can have a plurality of different positions each enabling a different stimulation signal (e.g., different amperage and/or frequency) to be provided to the conductive probe tip 102. For example, each of the different stimulation signals can be that from a respective conductor of the signal wire 112 or different circuit branch of the stimulation current conveying structure. Alternatively, as shown in FIG. 6, control switch 122 can include a potentiometer 123 for allowing a magnitude of the stimulation current to be selectively adjusted.

The conductive probe tip 102 can have one of many different shapes and signaling configurations. As shown, the conductive probe tip 102 has a substantially straight, monopolar configuration. Alternatively, the conductive probe tip 102 can have a bipolar signaling configuration (e.g., two parallel side-by-side probes or co-axial probe each connected to a respective stimulation signal providing circuit element/signal wire), a tripolar signaling configuration (e.g., three parallel side-by-side probes or tri-axial probe each connected to a respective stimulation signal providing circuit element/signal wire), an angled (i.e., bent) probe shape, a curved (i.e., arcuate) probe shape, or combinations thereof.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. An electrophysiological test stimulation probe apparatus, comprising:
   a conductive probe tip; and
   a stimulation probe handle assembly including a main body and a tip adjustment structure attached at a first end portion thereof to the main body, wherein the tip adjustment structure is rotatable with respect to the main body about a longitudinal axis of the main body, wherein the conductive probe tip is attached to a second end portion of the tip adjustment structure, wherein a first structural portion of the tip adjustment structure that comprises the first end thereof is pivotably attached to a second structural portion of the tip adjustment structure that comprises the second end portion thereof thereby allowing pivoting between said structural portions, wherein said structural portions of the tip adjustment structure are constrained to pivot about a transverse axis that is jointly defined by said structural portions of the tip adjustment structure and that extends perpendicularly through the longitudinal axis of the main body, wherein the first structural portion of the tip adjustment structure is attached to the main body for inhibiting movement thereof along the longitudinal axis whereby the transverse axis is located at a fixed position on the longitudinal axis over an entire range of pivoting of the second structural portion of the tip adjustment structure with respect to the first structural portion of the tip adjustment structure, and wherein the conductive probe tip is mounted on the second end portion of the tip adjustment structure so that the conductive probe tip pivots about the transverse axis in unison with an entire portion of the second structural portion of the tip adjustment structure when the second structural portion of the tip adjustment is pivoted about the transverse axis;
   wherein the first and second structural portions of the tip adjustment structure are jointly rotatable about the longitudinal axis of the main body independent of the conductive probe tip being pivoted with respect to the second portion of the tip adjustment structure;

wherein a first end portion of the first structural portion of the tip adjustment structure is attached to the main body to constrain movement of the first structural portion of the tip adjustment structure to rotation about the longitudinal axis; and wherein a second end portion of the first structural portion of the tip adjustment structure is attached to the second structural portion of the tip adjustment structure to constrain movement of the second structural portion of the tip adjustment structure with respect to the first structural portion of the tip adjustment structure to pivoting about the transverse axis.

2. The electrophysiological test stimulation probe apparatus of claim 1 wherein:
the stimulation probe handle assembly includes a stimulation current conveying structure electrically connected to the conductive probe tip; and
the stimulation current conveying structure includes an electrical continuity controller for enabling electrical continuity between the stimulation current conveying structure and the conductive probe tip to be selectively inhibited and enabled.

3. The electrophysiological test stimulation probe apparatus of claim 2 wherein the tip adjustment structure provides electrical continuity therethrough from the electrical continuity controller to the conductive probe tip.

4. The electrophysiological test stimulation probe apparatus of claim 3 wherein the stimulation current conveying structure maintains electrical continuity between the conductive probe tip and the electrical continuity controller over an entire range of rotation of the tip adjustment structure about the longitudinal axis of the main body and over an entire range of pivoting of the conductive probe tip about the transverse axis.

5. The electrophysiological test stimulation probe apparatus of claim 2 wherein the electrical continuity controller includes a potentiometer for enabling a magnitude of a stimulation current provided from the stimulation current conveying structure to the conductive probe tip to be selectively adjusted.

6. A stimulation probe apparatus, comprising:
a conductive probe tip having a first end portion and a second end portion;
a stimulation probe handle having a first end portion and a second end portion;
a tip adjustment structure including an interposer body and a probe tip mount, wherein the a first end portion of the interposer body is rotatably attached to the first end portion of the stimulation probe handle for enabling the tip adjustment structure to be rotated with respect to the stimulation probe handle about a longitudinal axis thereof, wherein the probe tip mount is pivotably attached to the interposer body for enabling the probe tip mount to be pivoted with respect to the interposer body about a pivot axis that is jointly defined by the interposer body and probe tip mount and that extends perpendicularly through the longitudinal axis, wherein the interposer body is attached to the stimulation probe handle for inhibiting movement thereof along the longitudinal axis whereby the pivot axis is located at a fixed position on the longitudinal axis over an entire range of pivoting of the probe tip mount with respect to the interposer body, and wherein the conductive probe tip is fixedly attached at the first end portion thereof to the probe tip mount so that the conductive probe tip pivots about the pivot axis in unison with an entire portion of the probe tip mount when the probe tip mount is pivoted about the pivot axis; and a stimulation current conveying structure mounted on the stimulation probe handle and electrically attached to the conductive probe tip for enabling a stimulation current to be provided thereto through the stimulation current conveying structure;

wherein the tip adjustment structure enables independent rotation of the interposer body and probe tip mount jointly about the longitudinal axis and pivoting of the probe tip mount about the pivot axis;

wherein a first end portion of the interposer body is attached to the main body to constrain movement of the interposer body to rotation about the longitudinal axis; and wherein a second end portion of the interposer body is attached to the probe tip mount to constrain movement of the probe tip mount with respect to the interposer body to pivoting about the transverse axis.

7. The stimulation probe apparatus of claim 6 wherein:
the stimulation current conveying structure includes an electrical continuity controller;
the electrical continuity controller enables electrical continuity between the stimulation current conveying structure and the conductive probe tip to be selectively inhibited and enabled; and
the electrical continuity controller includes a potentiometer for enabling a magnitude of a stimulation current provided from the stimulation current conveying structure to the conductive probe tip to be selectively adjusted.

8. The stimulation probe apparatus of claim 6 wherein:
the stimulation current conveying structure is integral with the tip adjustment structure for enabling electrical current to be provided to the conductive probe tip therethrough.

9. The stimulation probe apparatus of claim 6 wherein:
the stimulation current conveying structure includes an electrical continuity controller; and
the electrical continuity controller enables electrical continuity between the stimulation current conveying structure and the conductive probe tip to be selectively inhibited and enabled.

10. The stimulation probe apparatus of claim 9 wherein:
the stimulation current conveying structure is integral with the tip adjustment structure for enabling electrical current to be provided to the conductive probe tip therethrough.

* * * * *